United States Patent [19]

von Hoerschelmann et al.

[11] 4,397,952
[45] Aug. 9, 1983

[54] PROCESS FOR OBTAINING GLUCOSE DEHYDROGENASE AND MICRO-ORGANISM THEREFOR

[75] Inventors: Detlef von Hoerschelmann, Wielenbach; Hans Seidel, Tutzing; Gerhard Berger, Iffeldorf; Armin Masuth, Hamburg; Klaus Beaucamp, Tutzing; Wolfgang Gruber, Tutzing-Unterzeismering, all of Fed. Rep. of Germany

[73] Assignee: Boehringer Mannheim GmbH, Mannheim-Waldhof, Fed. Rep. of Germany

[21] Appl. No.: 260,480

[22] Filed: May 4, 1981

[30] Foreign Application Priority Data

May 21, 1980 [DE] Fed. Rep. of Germany ....... 3019450

[51] Int. Cl.³ .......................... C12N 9/04; C12Q 1/32; C12R 1/085
[52] U.S. Cl. .................................... 435/190; 435/26; 435/834
[58] Field of Search .................................. 435/190, 26

[56] References Cited

U.S. PATENT DOCUMENTS

4,120,755  10/1978  Pierre et al. ..................... 435/26 X

OTHER PUBLICATIONS

Warth, Journal of Bacteriology, vol. 143, No. 1, pp. 27–34, Jul. 1980.
Kuan et al., Clinical Chemistry, vol. 23, No. 6, pp. 1058–1061 (1977).
Sadoff, Methods in Enzymology, vol. 9, pp. 103–107 (1966).

*Primary Examiner*—Lionel M. Shapiro
*Attorney, Agent, or Firm*—Felfe & Lynch

[57] ABSTRACT

The present invention provides a process for obtaining glucose dehydrogenase by culturing a micro-organism in an appropriate nutrient medium and obtaining the enzyme from the cell mass or from the culture medium, wherein the micro-organism cultured is *Bacillus cereus* DSM 1644. The nutrient medium used contains a carbon source which consists predominantly or solely of glycerol.

4 Claims, No Drawings

PROCESS FOR OBTAINING GLUCOSE DEHYDROGENASE AND MICRO-ORGANISM THEREFOR

This invention relates to a process for obtaining glucose dehydrogenase and to a new micro-organism especially suited for this purpose.

Glucose dehydrogenase (Gluc-DH) (E.C.1.1.1.47) catalyses the following reaction:

$\beta$-D-glucose + NAD $\xrightarrow{\text{Gluc-DH}}$ D-gluconolactone + NADH$_2$ Since NADH$_2$ can easily be determined, this reaction can be used for the analytical determination of glucose.

A disadvantage of this process is that the enzyme has hitherto been difficult to obtain and was, therefore, very expensive. This is due, on the one hand, to disturbing impurities which are difficult to remove (resistant spores, NADH oxidases) and, on the other hand, to too low yields. It is admittedly known (see "Abstracts of the 5th International Fermentation Symposium," Berlin, 1976, page 260) to suppress spore formation by culturing *Bacillus megaterium* M 1286, the yield thereby being said to be about 2 U/ml. However, our own experiments gave a yield of at most 0.25 U/ml. and very high contamination with NADH oxidases.

It is also known to use a strain of *Bacillus cereus* which, however, only produces about 0.1U glucose-dehydrogenase/ml. of culture and displays very considerable spore formation.

It is an object of the present invention not only to improve the known process for obtaining glucose dehydrogenase, especially with regard to enzyme yield, but also with regard to sporulation (spore formation up to the formation of maximum glucose dehydrogenase activity is undesired), as well as elimination of interfering activities, especially of NADH oxidases.

Thus, according to the present invention, there is provided a process for obtaining glucose dehydrogenase by culturing a micro-organism in an appropriate nutrient medium and obtaining the enzyme from the cell mass or from the nutrient medium, wherein the micro-organism cultured is *Bacillus cereus* DSM 1644.

The micro-organism *Bacillus cereus* DSM 1644 used in the process according to the present invention is new and is obtained by a mutation process involving a suitable parent strain. *Bacillus cereus* DSM 1730 is the preferable parent strain but *Bacillus cereus* DSM 345 and *Bacillus cereus* ATCC 10987 also proved to be useful.

For mutation, the parent strain is incubated in the presence of methyl or ethyl methanesulphonate for 10 to 90 minutes at 28° C. Mutagenesis is then stopped by washing in phosphate buffered saline and single clones of mutagen treated cells are isolated in surface culture. With these, overnight cultures are prepared which, after incubation for 12 hours, are examined microscopically to obtain asynchronous cultures in which spore-free, endospore-containing cells, as well as the first free spores, are visible. These are simultaneously selected and used for a fresh batch. After 5 to 7 growth cycles a pure culture of *Bacillus cereus* DSM 1644 was obtained, which is also the subject of the present invention.

The micro-organism according to the present invention is a lad-mutant (late abnormal development), the spore development of which proceeds normally up to developmental stage III but which is then inhibited for up to about 20 hours, whereafter it resumes development until the appearance of heat-resistant spores.

According to a taxonomic description the microorganism consists of individual cells with a tendency to chain formation. The cell size is $1 \times 4$ to $6\mu$ (growth-phase dependent). The spores have an oval shape and are terminally arranged. Gram positive. Growth at 25° to 40° C. in aerobic or anaerobic condition. $\beta$-Haemolysis on blood agar. Further positive reactions include: glucose, maltose, salicin, nitrate, Voges-Proskauer, citrate and catalase. Negative tests are indole, oxidase, lysine decarboxylase, lactose, arabinose, saccharose, mannose and xylose. The definition of the growth phases corresponds to that given in Biochem. J., 109, 819/1968, and in Adv. Genet., 18, 69/1976.

For the culturing, there can be used the known nutrient media which are suitable for the genus Bacillus. A nutrient medium is preferred in which the carbon source consists of glycerol instead of glucose. An especially preferred nutrient medium contains, per liter:

5 to 50 g. glycerol,
1 to 10 g. yeast extract,
1 to 50 g. peptone,
1 to 20 g. ammonium sulphate,
0.2 to 5 g. dipotassium phosphate,
0.1 to 5 g. magnesium sulphate,
1 to 10 g. sodium chloride, as well as trace elements (manganese, zinc, copper, calcium and iron).

The pH is adjusted to a value of from 7 to 8, preferably by the addition of an aqueous solution of sodium hydroxide.

To achieve maximum glucose dehydrogenase activity, aerobic growth is carried out for 12 to 20 hours at 30° C., After centrifugation the supernatant is discarded while the enzyme is obtained from the biomass.

Normally, the glucose dehydrogenase is found intracellularly and the harvested cells are, therefore, disrupted by methods conventionally used to prepare a cell-free extract. Appropriate methods for this purpose include ultrasonic treatment, lysozyme digestion, glass bead disruption (Vibrogen Mill) and the like. The maximum enzyme yield is 2000 U/liter of culture medium. Further purification can be carried out by known methods, for example, as described in J. Bacteriol., 132, 282–293/1977.

An special advantage of the process according to the present invention is that, as a result of retarded sporulation, which, during growth until harvest does not lead to the formation of heat-resistant spores, contamination problems are avoided. This substantially simplifies the culturing and obtaining of the enzyme.

In contrast thereto, using parent strain *Bacillus cereus* DSM 1730, massive sporulation occurs already after 15 hours and the biomass obtained therefrom always contains a considerable amount of heat-resistant spores.

This shows that, according to the present invention, the enzyme yield can be increased and, at the same time, the process is substantially simplified. An additional advantage is that undesired enzyme activities, especially NADH oxidase activity, which is particularly undesirable when the enzyme is used for determining glucose, can be separated off very easily, for example by a heating step.

The following Example is given for the purpose of illustrating the present invention:

EXAMPLE

A nutrient medium of the following composition:

2.8 g. yeast extract,
4 g. ammonium sulphate,
1.0 g. dipotassium phosphate,
0.8 g. magnesium sulphate,
4.8 g. sodium chloride,
5 g. glycerol (87%).
1.6 g. peptone, as well as
trace amounts of manganese sulphate, zinc sulphate, copper sulphate, calcium chloride and ferric chloride (pH 7.4), was sterilized and then inoculated with *Bacillus cereus* DSM 1644. After incubating for 8 hours at 30° C., the medium of the main culture, having the same composition as above, was inoculated with 1% of pre-culture and aerated. The main culture was cultured for 19 hours at 30° C., with aeration and shaking. Determination of glucose dehydrogenase at this time gave an activity of 1800 U/liter. The cell mass was then centrifugated and frozen. After thawing cells were disrupted by ultrasonic treatment and a clear solution was obtained by centrifugation.

The activity determination was carried out in the following manner:

Enzyme assay:
2.1 ml. 0.05 M tris-manganese buffer + 12 mg./liter manganese sulphate hydrate (pH 8.5),
0.3 ml. 1 M glucose solution
0.4 ml. NAD solution (10 mg./ml.)

The reaction was started by the addition of sample (crude extract). Temperature 25° C.; the increase of extinction was measured at 365 nm.

It will be understood that the specification and examples are illustrative but not limitative of the present invention and that other embodiments within the spirit and scope of the invention will suggest themselves to those skilled in the art.

What is claimed is:

1. Process for obtaining glucose dehydrogenase which comprises culturing the micro-organism *Bacillus cereus* DSM 1644 in a nutrient medium and obtaining glucose dehydrogenase from the cell mass or from the culture medium.

2. Process as claimed in claim 1 wherein the carbon source of the nutrient medium consists predominantly or solely of glycerol.

3. Process as claimed in claim 2 wherein the nutrient medium contains, per liter:
5 to 50 g. glycerol,
1 to 10 g. yeast extract,
1 to 50 g. peptone,
1 to 20 g. ammonium sulphate,
0.2 to 5 g. diptassium phosphate,
0.1 to 5 g. magnesium sulphate,
1 to 10 g. sodium chloride,
as well as trace elements.

4. A biologically pure culture of *Bacillus cereus* DSM 1644.

* * * * *